(12) United States Patent
Lazar

(10) Patent No.: US 11,179,509 B2
(45) Date of Patent: *Nov. 23, 2021

(54) SYSTEM AND METHOD FOR DETECTING DIALYSIS NEEDLE DISLODGMENT

(71) Applicant: Andrew Lazar, Pepper Pike, OH (US)

(72) Inventor: Andrew Lazar, Pepper Pike, OH (US)

( * ) Notice: Subject to any disclaimer, the term of this patent is extended or adjusted under 35 U.S.C. 154(b) by 71 days.

This patent is subject to a terminal disclaimer.

(21) Appl. No.: 16/390,609

(22) Filed: Apr. 22, 2019

(65) Prior Publication Data

US 2019/0255244 A1 Aug. 22, 2019

Related U.S. Application Data

(63) Continuation-in-part of application No. 15/994,052, filed on May 31, 2018, now Pat. No. 11,000,640.

(60) Provisional application No. 62/576,481, filed on Oct. 24, 2017.

(51) Int. Cl.
*A61M 1/14* (2006.01)
*A61M 1/36* (2006.01)

(52) U.S. Cl.
CPC .......... *A61M 1/3656* (2014.02); *A61M 1/14* (2013.01); *A61M 1/3661* (2014.02); *A61M 2205/18* (2013.01); *A61M 2205/3313* (2013.01); *A61M 2205/3317* (2013.01); *A61M 2205/3592* (2013.01); *A61M 2205/581* (2013.01); *A61M 2205/582* (2013.01); *A61M 2205/583* (2013.01)

(58) Field of Classification Search
CPC .... A61M 1/3656; A61M 1/14; A61M 1/3661; A61M 2205/18; A61M 2205/3592; A61M 2205/3313; A61M 2205/581; A61M 2205/582; A61M 2205/583; A61M 2205/3317; A61M 2039/1005

See application file for complete search history.

(56) References Cited

U.S. PATENT DOCUMENTS

| | | | |
|---|---|---|---|
| 2006/0130591 A1* | 6/2006 | Perkins | A61M 1/3655 73/800 |
| 2007/0219480 A1* | 9/2007 | Kamen | G01F 22/00 604/20 |
| 2009/0082647 A1 | 3/2009 | Busby | |
| 2009/0082649 A1* | 3/2009 | Muller | A61M 1/3659 600/310 |
| 2011/0232388 A1* | 9/2011 | Butterfield | A61B 5/021 73/705 |

(Continued)

*Primary Examiner* — Theodore J Stigell
*Assistant Examiner* — Daniel Moore
(74) *Attorney, Agent, or Firm* — Rankin, Hill & Clark LLP

(57) ABSTRACT

A system for detecting needle dislodgement includes a first sensor element and a second sensor element. The first sensor element is attached to a first associated dialysis tubing having a needle connected at one end offset from the needle and a sterile field, which is an area on a leg or arm adjacent to where the needle is inserted, such that movement of the first associated dialysis tubing results in movement of the first sensor element. The second sensor element attaches to a second associated dialysis tubing having a needle connected at one end and detects movement of the first sensor element with respect to the second sensor element. An alarm is in communication with the first or second sensor element and generates a signal when the movement of the first sensor element with respect to the second sensor element is outside a predetermined threshold.

14 Claims, 9 Drawing Sheets

(56) References Cited

U.S. PATENT DOCUMENTS

2016/0334246 A1\* 11/2016 Haupt ................... G01D 5/245
2017/0333623 A1\* 11/2017 Kamen ............... A61M 5/1458

\* cited by examiner

SYSTEM AND METHOD FOR DETECTING DIALYSIS NEEDLE DISLODGMENT

BACKGROUND

Dialysis involves the removal of blood from a patient and the return of the blood after it has been cleaned by a dialysis machine. Typical dialysis treatments require two needles: one needle for the withdrawal of blood and one needle for the return of blood to the patient. The withdrawal site is normally an artery. A needle connected with dialysis tubing and a pump are used to draw blood from the artery to the dialysis machine. It can be relatively simple to detect needle dislodgement from the artery using conventional air sensor technology. If air is being drawn through the pump, this can be detected and an alarm can be sounded to indicate needle dislodgement from the artery. The return line includes a needle with venous access connected with dialysis tubing. If the venous needle becomes dislodged, the pump would typically not detect air and may continue to operate and continue to draw blood from the patient.

A known device for detecting needle dislodgement, and especially venous needle dislodgement, is described in US 2006/00130591. This known device can include a venous needle equipped with a photo sensor that is covered with an opaque patch. If the venous needle becomes dislodged, the photo sensor is exposed to light, which can then result in a signal being transmitted to provide an alarm to the patient. Such a device is not particularly suitable for patients who cover their arm with a blanket or who perform nocturnal dialysis while sleeping in a dark bedroom.

Another known device described in US 2009/0082647 includes an access needle assembly including a butterfly mount, tubing, a venous access needle, a sleeve made from clear tubing, and an imbedded wire. The butterfly mount includes a detector circuit to detect the wire within the tubing. The sleeve is an electroactive sleeve that contains a metallic or magnetic component that is detectable by a proximity or Hall-effect sensor. The butterfly mount and the detector circuit are provided in the sterile field, which is near the venous needle entry point and thus requires sterilization prior to insertion of the venous access needle.

SUMMARY

In view of the foregoing, a system for detecting needle dislodgement includes a first sensor element, a second sensor element, and an alarm. The first sensor element is configured to attach to a first associated tubing having a needle connected at one end. The first sensor element is attached to the first associated tubing offset from the needle and a sterile field, which is an area on a leg or arm adjacent to where the needle is inserted. The first sensor element is attached to the first associated tubing in a manner such that movement of the first associated tubing results in movement of the first sensor element.

The second sensor element is configured to attach to a second associated tubing having a needle connected at one end. The second sensor element detects movement of the first sensor element with respect to the second sensor element. The alarm is in communication with the second sensor element and generates a signal when the movement of the first sensor element with respect to the second sensor element is outside a predetermined threshold. In another embodiment, the alarm is also in communication with the first sensor element. The signal can be a light, a buzzer, a voice recording, a vibration, a text, or a wireless message to a central system.

The first sensor element may be attached to the first associated tubing via a first clip, and the second sensor element may be attached to the second associated tubing via a second clip. In one embodiment, the first sensor element is a magnet, and the second sensor element is one or more Hall-effect sensors, one or more magnetometers, or a combination of Hall-effect sensors and magnetometers. In another embodiment, the first sensor element is a light source, and the second sensor element is one or more photo resistors, one or more infrared light receiver, or any combination of photo resistors and infrared light receivers. In still another embodiment, the first sensor element is a line of sight emitter, and the second sensor element is a line of sight receiver.

The system may further include a controller in electrical communication with the second sensor element. The controller generates a signal to an associated dialysis machine to disable a pump on the associated dialysis machine when the movement of the first sensor element with respect to the second sensor element is outside a predetermined threshold. The alarm and controller may be positioned in a housing. In the embodiment with the housing, the second sensor element is connected to the housing via a first wire. The first wire may be receivable in the housing and adjustable in length. In another embodiment, the first sensor element is connected to the housing via a second wire.

A method for detecting a needle dislodgement includes attaching a first sensor element to a first associated tubing having a needle at one end in a manner such that the first sensor element is offset from the needle. A second sensor element is attached to a second associated tubing having a needle at one end in a manner such that the second sensor element is offset from the needle. The needle and the needle are inserted into a patient at a sterile field. The sterile field is an area on a leg or arm of a patient adjacent to where the needle is to be inserted. The movement of the first sensor element with respect to the second sensor element is monitored via a controller and an alarm circuit. When the movement of the first sensor element with respect to the second sensor element is outside a predetermined threshold, an alarm signal is generated via the controller or the alarm circuit indicating a potential dislodgement of the needle.

Attaching the first sensor element to the first associated tubing may further include attaching a first clip carrying the first sensor element to the first associated tubing offset form the needle along the length of the first associated tubing. Likewise, attaching the second sensor element to the second associated tubing may further include attaching a second clip carrying the second sensor element to the second associated tubing offset from the needle along the length of the second associated tubing. The method may further include electrically connecting the second sensor element to the controller via a first wire. The method may also comprise automatically stopping a pump of a dialysis machine when the movement of the first sensor element with respect to the second sensor element is outside a predetermined threshold.

DETAILED DESCRIPTION

Figure 1:
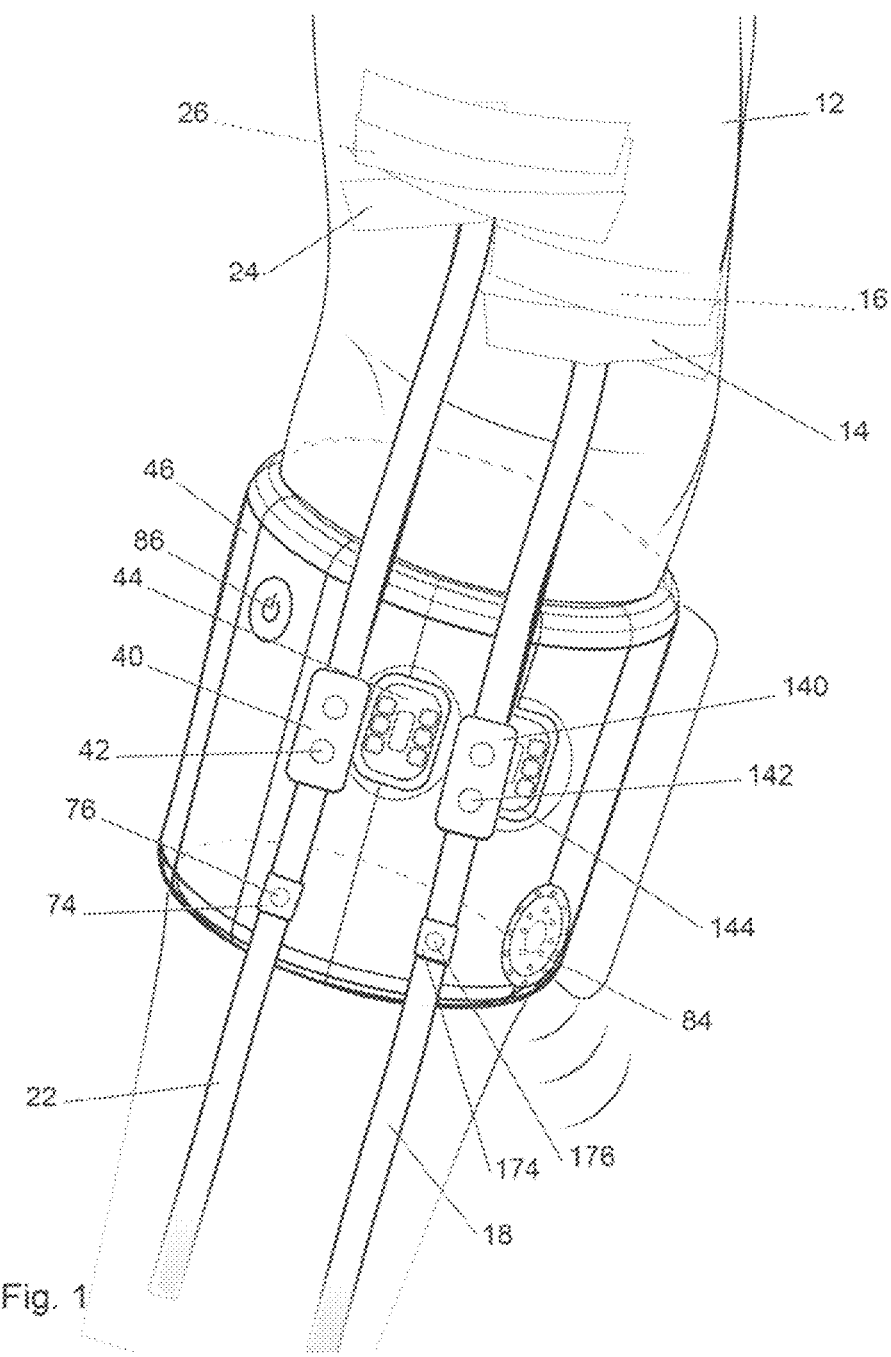
FIG. 1 is a schematic view of a system for detecting needle dislodgement.

FIG. 1 generally depicts a system 10 for detecting needle dislodgement. The system 10 will be described with reference to a dialysis treatment; however, the system 10 can be used to detect needle dislodgement from a patient undergoing other treatments. In FIG. 1, a needle (not visible) is inserted into a fistula in a patient's arm 12 on an arterial side of the fistula and is shown covered by tape 14. The area of the arm 12 adjacent to where the needle is inserted is referred to as a sterile field 16, which needs to be cleaned and sterilized prior to insertion of the needle into the arm 12. The needle is attached at one end to a withdrawal line dialysis tubing 18 which is attached to a dialysis machine (not shown). Blood is drawn from the needle connected with the withdrawal line dialysis tubing 18 and transported through a pump (not shown) to a dialysis machine, and then returned to the patient through return line dialysis tubing 22 having a needle (not visible) connected at one end, which is covered by tape 24. The needle connected with the return line dialysis tubing 22 enters the arm at a venous access sterile field 26 on a venous side of the fistula.

The portion of the system 10 to detect whether the venous needle, which is covered by the tape 24, becomes dislodged will now be described. A first sensor element mount 40 attaches to the return line dialysis tubing 22 offset from the needle, which is hidden under the tape 24, along the length of the return line dialysis tubing 22 in a manner such that movement of the return line dialysis tubing 22 results in movement of the first sensor element mount 40. When attached to the return line dialysis tubing 22, the first sensor element mount 40 is inhibited from movement with respect to the return line dialysis tubing 22. In other words, if the return line dialysis tubing 22 moves, then the first sensor element mount 40 moves with it. As one example, the first sensor element mount 40 can be a U-shaped clip, or a similar clip or device, that can fasten onto the return line dialysis tubing 22 while not impeding the flow of blood through the return line dialysis tubing 22.

A first sensor element 42 mounts to the first sensor element mount 40 in a manner such that movement of the first sensor element mount 40 results in movement of the first sensor element 42. The first sensor element 42 can be a magnet or other component of a proximity sensor that cooperates with a second sensor element 44 mounted to a non-sterile sensor mounting apparatus 46. The non-sterile sensor mounting apparatus 46 is configured to secure to the arm 12, or even a leg, of the patient undergoing dialysis treatment. The non-sterile sensor mounting apparatus 46 is configured to secure to the arm 12 or leg offset from the venous access sterile field 26. As such, the non-sterile sensor mounting apparatus 46 and the components mounted thereto need not be sterilized when performing dialysis treatment. In the embodiment depicted in FIG. 1, the non-sterile sensor mounting apparatus 46 is a cuff or band, which can be similar to a blood pressure cuff without the inflatable bladder, having hook and loop fasteners for securing to the arm 12 or leg of the patient.

As mentioned above, the second sensor element 44 mounts to the non-sterile sensor mounting apparatus 46. As such, the second sensor element 44 is configured to secure to an arm or leg offset from the venous access sterile field 26. The second sensor element 44 is attached to the non-sterile sensor mounting apparatus 46 such that movement of the non-sterile sensor mounting apparatus 46 results in movement of the second sensor element 44. Where the first sensor element 42 is a magnet, the second sensor element 44 can be a Hall-effect sensor. In the embodiment illustrated in FIG. 1, the first sensor element 42 is configured to be positioned above the second sensor element 44 and the second sensor element 44 is configured to be positioned between the first sensor element 42 and the arm 12 (or leg) when the non-sterile sensor mounting apparatus 46, which can be a cuff, is secured to the arm 12 (or leg) and the needle at the one end of the return line dialysis tubing 22 is inserted into the venous access sterile field 26. The first sensor element 42 need not necessarily cover the second sensor element 44, but instead could be offset from but still above the second sensor element 44 in relation to the arm 12 (or leg) to facilitate placement of the return line dialysis tubing 22.

Figure 2:
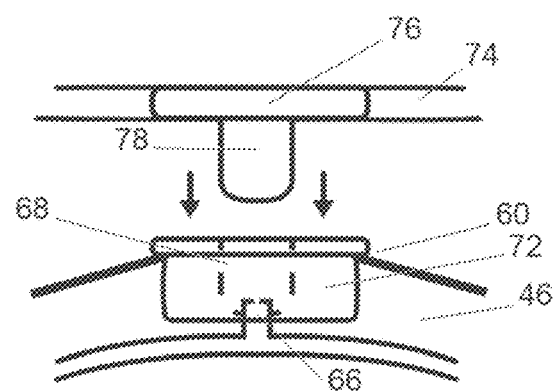
FIG. 2 is a side schematic view of a portion of the system for detecting needle dislodgement depicted in FIG. 1.
Figure 3:
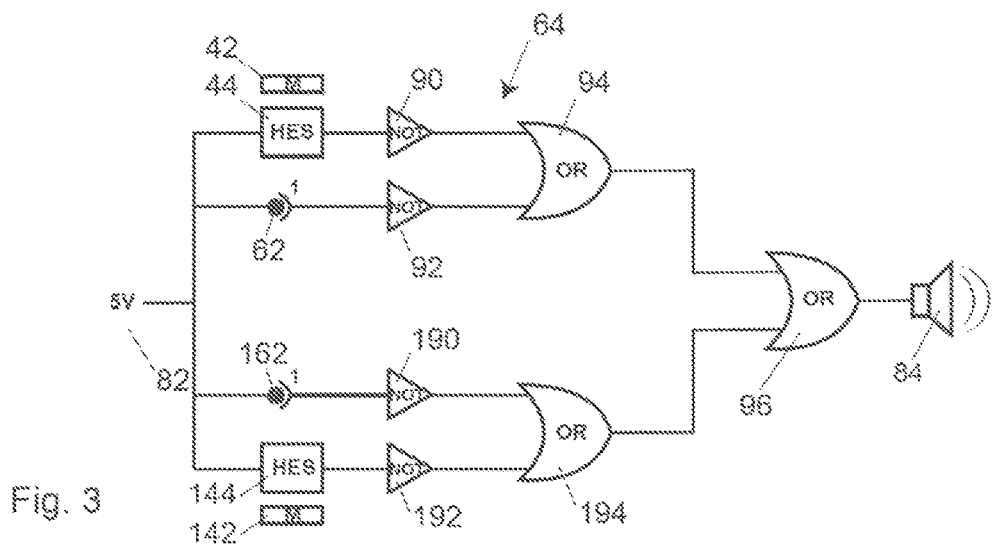
FIG. 3 is a diagram of an alarm circuit for the system for detecting needle dislodgement.

With reference to FIG. 2, a third sensor element 60 can mount to the non-sterile sensor mounting apparatus 46. In the illustrated embodiment, the third sensor element 60 is a contact switch 62, which is also shown in FIG. 3, which depicts an example of alarm circuit 64, which will be described in more detail below. With reference back to FIG. 2, the third sensor element 60 can include a movable contact 66 positioned in a cavity 68 of an actuator receptacle 72, which can be fixed to the non-sterile sensor mounting apparatus 46. With reference back to FIG. 1, a retainer 74, which can be smaller than but similar in configuration to the first sensor element mount 40, attaches to the return line dialysis tubing 22 offset from the needle (disposed beneath the tape 24) and offset from the first sensor element mount 40. The retainer 74 can be a clip that affixes to the return line dialysis tubing 22 in a manner such that movement of the return line dialysis tubing 22 results in movement of the retainer 74. With reference to FIG. 2, a fourth sensor element 76, which can be in the form of an actuator such as a snap-in button, connects with the retainer 74 for movement with the retainer 74. The fourth sensor element 76 includes an extension 78 that is configured to be received inside the cavity 68 provided in the actuator receptacle 72. When the extension 78 is received inside the cavity 68, the extension 78 contacts the movable contact 66 so as to close the contact switch 62 (FIG. 3).

With reference to FIG. 3, the alarm circuit 64 that is depicted is configured to generate a signal indicative of a position of the first sensor element 42 with respect to the second sensor element 44. The alarm circuit 64 is also configured to generate a signal indicative of a position of the fourth sensor element 76 with respect to the third sensor element 60. A power source 82, such as a small voltage battery, can be provided on the non-sterile sensor mounting apparatus 46. The power source 82 connects with the second sensor element 44, which can be a Hall-effect sensor. When the second sensor element 44 detects the presence of the first sensor element 42, which can be a magnet, the return line dialysis tubing 22 is in an appropriate position such that no needle dislodgement is detected. If the needle connected with the return line dialysis tubing becomes dislodged, the first sensor element 42 moves with respect to the second sensor element 44, such that the second sensor element 44 no longer detects the magnetic field of the first sensor element 42, which can result in power being delivered to a speaker 84, which is part of the alarm circuit 64. An on/off switch 86, which can also be mounted to the non-sterile sensor mounting apparatus 46 and is not depicted in the alarm circuit 64 diagram in FIG. 2, can also be provided to turn the alarm circuit 64 on and off. The alarm circuit 64 depicted in FIG. 3 also includes the contact switch 62 in electrical communication with the speaker 84. The alarm circuit can include NOT gates 90, 92 and OR gates 94, 96 to allow either movement of the first sensor element 42 with respect to the second sensor element 44 or movement of the fourth sensor element 76 with respect to the movable contact 66, which is part of the third sensor element 60, to generate an alarm signal, for example through the speaker 84.

Other indicators other than a speaker 84 can also be provided. For example, a light could be illuminated. Additionally, a wireless signal generator could be provided in addition to or in lieu of the speaker 84 to wirelessly communicate with another device, such as a smart phone or the dialysis machine, and the smart phone or dialysis machine can receive the signal and generate an appropriate indicative signal for the patient undergoing dialysis to indicate that the needle has dislodged. Additionally, the alarm circuit 64 could also provide a signal to the dialysis machine to turn off the pump when either movement of the first sensor element 42 with respect to the second sensor element 44 or movement of the fourth sensor element 76 with respect to the movable contact 66 is detected.

With reference back to FIG. 1, the portion of the system 10 to detect whether the arterial needle, which is covered by the tape 14, can include the same components as the portion of the system 10 to detect whether the venous needle has dislodged. A first arterial sensor element mount 140 can attach to the withdrawal line dialysis tubing 18 offset from the arterial needle, which is not visible underneath the tape 14, in a manner such that movement of the withdrawal line dialysis tubing 18 results in movement of the first arterial sensor element mount 140. The first arterial sensor element mount 140 is also inhibited from movement with respect to the withdrawal line dialysis tubing 18 when attached to the withdrawal line dialysis tubing 18. The first arterial sensor element mount 140 can be identical to the first sensor element mount 40 described above.

A first arterial sensor element 142 mounts to the first arterial sensor element mount 140 in a manner such that movement of the first arterial sensor element mount 140 results in movement of the first arterial sensor element 142. The first arterial sensor element 142 can be identical to the first sensor element 42 and cooperate with a second arterial sensor element 144 mounted to the non-sterile sensor mounting apparatus 46 in the same manner that the first sensor element 42 cooperates with the second sensor element 44. The non-sterile sensor mounting apparatus 46 is configured to secure to the arm 12 or leg also offset from the sterile field 16 for the arterial needle.

The second arterial sensor element 144 can be identical to the second sensor element 44 and mounts to the non-sterile sensor mounting apparatus 46. The second arterial sensor element 144 is attached to the non-sterile sensor mounting apparatus 46 such that movement of the non-sterile sensor mounting apparatus 46 results in movement of the second arterial sensor element 144.

A third arterial sensor element (not visible but identical to the third sensor element 60) can mount to the non-sterile sensor mounting apparatus 46. The third arterial sensor element can be a contact switch 162, which is also shown in FIG. 3. The third arterial sensor element can include a moveable contact (identical to the movable contact 66) positioned in a cavity of an actuator receptacle, which can be fixed to the non-sterile sensor mounting apparatus 46. With reference back to FIG. 1, an arterial line retainer 174, which can be to the retainer 74, attaches to the withdrawal line dialysis tubing 18 offset from the needle (disposed beneath the tape 14) and offset from the first arterial sensor element mount 140. The arterial line retainer 174 can be a clip that affixes to the withdrawal line dialysis tubing 18 in a manner such that movement of the withdrawal line dialysis tubing 18 results in movement of the arterial line retainer 174. A fourth arterial sensor element 176, which can be in the form of a snap-in button, connects with the arterial line retainer 174 for movement with the arterial line retainer 174. The fourth arterial sensor element 176 includes an extension (not visible in FIG. 1, but identical to the extension 78 in FIG. 2) that is configured to be received inside the cavity provided in the actuator receptacle. When the extension is received inside the cavity, the extension contacts the moveable contact so as to close the contact switch 162 (FIG. 3).

With reference to FIG. 3, the alarm circuit 64 can include NOT gates 190, 192 and OR gates 194, 96 to allow either movement of the first arterial sensor element 142 with respect to the second arterial sensor element 144 or movement of the fourth arterial sensor element 176 with respect to the movable contact to generate an alarm signal, for example through the speaker 84.

Figure 4:
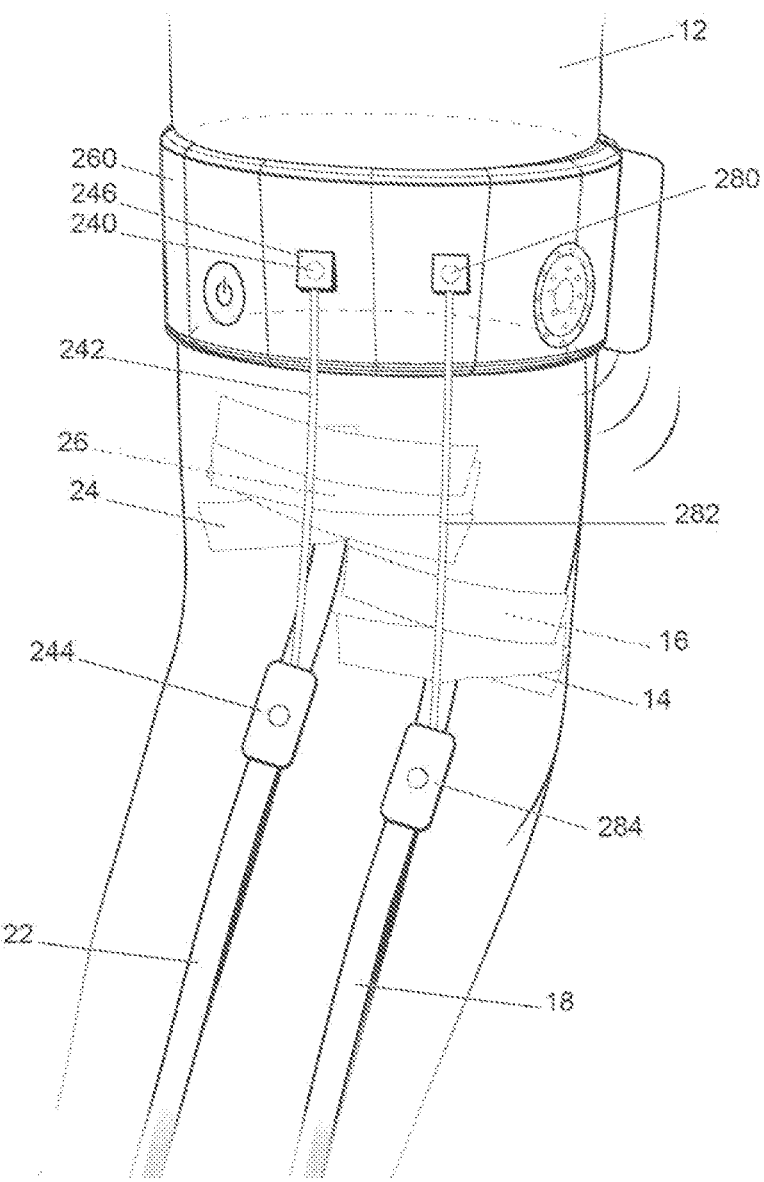
FIG. 4 is a perspective view of another system for detecting needle dislodgement.
Figure 5:
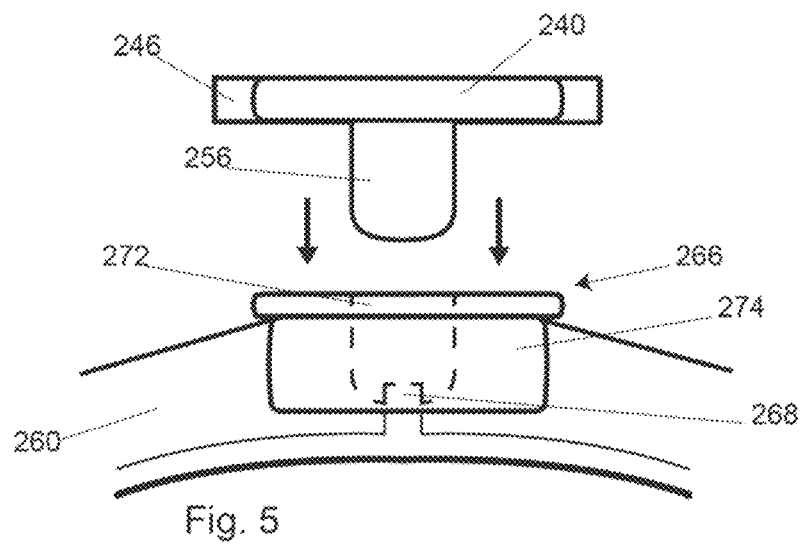
FIG. 5 is a side schematic view of a portion of the system for detecting needle dislodgement depicted in FIG. 4.

FIGS. 4 and 5 depict an alternative arrangement of a system 210 for detecting needle dislodgement. The system 210 includes a first sensor element 240 that attaches to the return line dialysis tubing 22 offset from the needle, which is disposed beneath the tape 24, through a tether 242, which connects with a tether connector 244. Movement of the return line dialysis tubing 22 results in movement of the first sensor element 240 due to the connection between the first sensor element 240 and the tether connector 244, which is fixed to the return line dialysis tubing 22.

The first sensor element 240 attaches to a retainer 246 which can be similar to the retainer 74 described above. The first sensor element 240 can be an actuator in the form of a snap-in button having an extension 256 similar to the extension 78 described above with reference to FIG. 3.

A non-sterile sensor mounting apparatus 260, which can be similar to the non-sterile sensor mounting apparatus 46 described above, is configured to secure to the arm 12 or a leg of the patient undergoing dialysis treatment. The non-sterile sensor mounting apparatus is configured to secure to the arm 12 or a leg of the patient offset from the sterile fields

16, 26. As illustrated, the non-sterile sensor mounting apparatus 260 in FIG. 4 is a cuff, which has been described above in more detail.

A second sensor element 266 mounts to the non-sterile sensor mounting apparatus 260. The second sensor element 266 in the embodiment depicted in FIGS. 4 and 5 can be a contact switch similar to the third sensor element 60 described above. The second sensor element 266 can include a moveable contact 268 similar to the movable contact 66 described above. The moveable contact 268 can be positioned within a cavity 272 provided in a button receptacle 274.

In addition to including components to detect dislodgement of the venous needle, the system 210 can detect dislodgement of the arterial needle, if desired. The system can include a first arterial sensor element 280 that attaches to the withdrawal line dialysis tubing 18 offset from the arterial needle, which is disposed beneath the tape 14, through a tether 282, which connects with a tether connector 284. Movement of the withdrawal line dialysis tubing 18 results in movement of the first arterial sensor element 280 due to the connection between the first arterial sensor element 280 and the tether connector 284, which is fixed to the withdrawal line dialysis tubing 18.

The first arterial sensor element 280 attaches to a retainer 286 which can be similar to the retainer 74 described above. The first arterial sensor element 280 is identical to first sensor element 240 in the illustrated embodiment. A second arterial sensor element (not visible), which is identical to the second sensor element 266 in the illustrated embodiment, mounts to the non-sterile sensor mounting apparatus 260.

In use, the patient inserts the arterial needle (not visible) at the sterile field 16 and covers the needle with tape 14. The patient then inserts the venous needle at the venous access sterile field 26 and covers the venous needle with the tape 24. The non-sterile sensor mounting apparatus 260 can then be secured to the arm 12 (or the leg) of the patient undergoing dialysis treatment outside of each sterile field 16, 26. The tether connector 244 can then be connected to the return line dialysis tubing 22 or can be already attached to the return line dialysis tubing 22 offset from the respective needle. The first sensor element 240 can then be inserted into the button receptacle 274 such that the extension 256 is received within the cavity 272. The extension 256 can then contact the moveable contact 268, thus closing an alarm circuit, which is not shown but can take a similar configuration to the alarm circuit 64 shown in FIG. 3. The same procedure can be followed with the first arterial sensor element 280. As such, if the first sensor element 240 moves with respect to the second sensor element 266 (or first arterial sensor element 280 moves with respect to the second arterial sensor element) a signal is generated and alarm can be provided to the patient.

Figure 6:
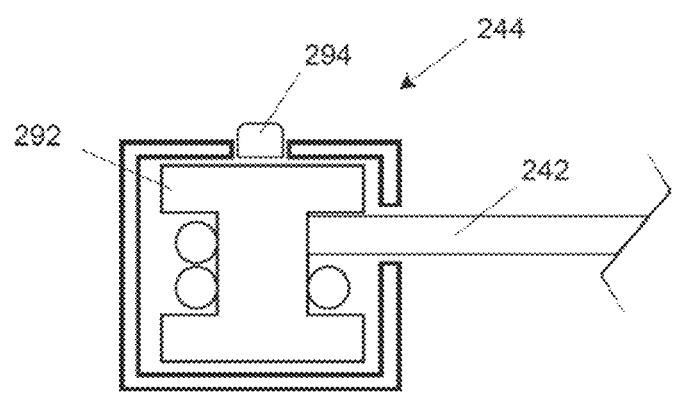
FIG. 6 is a schematic depiction of a tether connector for the system for detecting needle dislodgement depicted in FIG. 4 where a length of the tether is adjustable.
Figure 7:
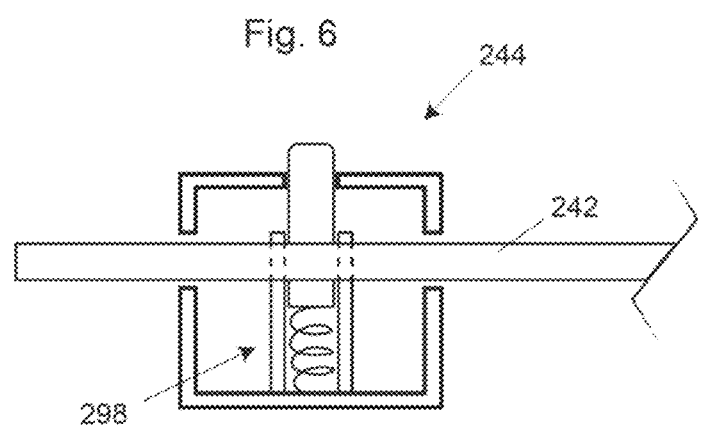
FIG. 7 is a schematic depiction of another tether connector for the system for detecting needle dislodgement depicted in FIG. 4 where the length of the tether is adjustable.

The tethers 242, 282 can be adjustable in length. FIG. 6 is a schematic depiction of the tether connector 244, and the tether connector 284 can have a similar configuration. The tether 242 can wind around a wheel 292, which is positioned in the tether connector 244 and can be biased by a torsion spring (not shown) so as to retract the tether 242 within the tether connector 244 around the wheel 292. A button 294 or a similar movable component that can be actuated by an operator is operatively connected to the wheel 292 to preclude rotation of the wheel 292 after the adjustment of the length of the tether 242 to a desired length. Alternatively and with reference to FIG. 7, the tether 242 could extend through the tether connector 244 and a clamping mechanism 298 could be provided to adjust the length of the tether 242.

Figure 8:
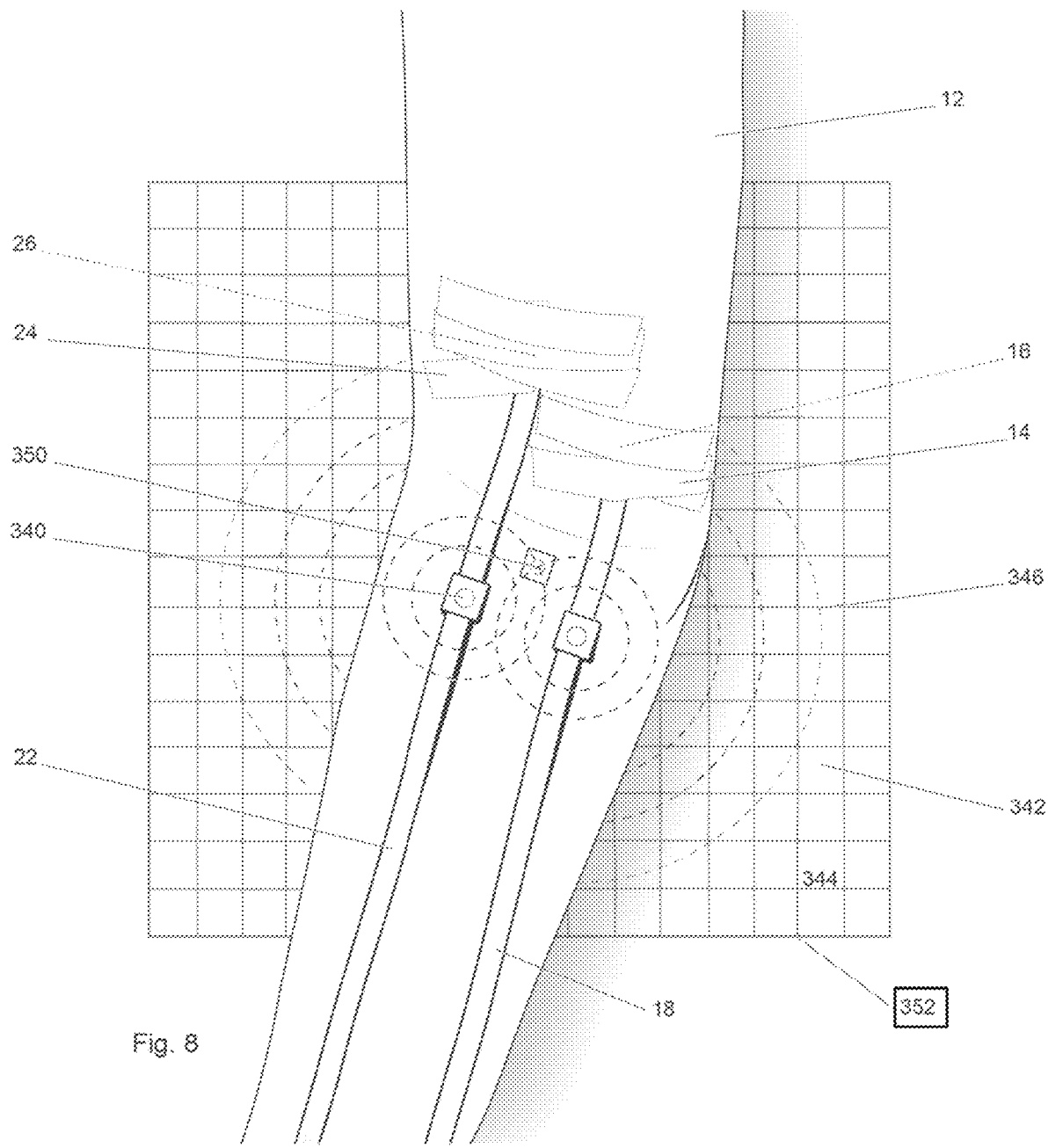
FIG. 8 is a schematic view of another system for detecting needle dislodgement.

FIG. 8 depicts another embodiment of a system for detecting needle dislodgement in which a first sensor element 340 attaches to the return line dialysis tubing 22 offset from the needle (hidden by the tape 24) in a manner such that movement of the return line dialysis tubing 22 results in movement of the first sensor element 340.

In this embodiment, an array board 342 is configured to support the arm 12 (or leg) of a patient undergoing dialysis treatment. In this embodiment, the array board 342 is also configured to support the arm 12 (or leg) offset from the sterile fields 16, 26 in that the patient's arm 12 or leg rests on the array board 342 with the sterile fields 16, 26 spaced from an upper surface 344 of the array board 342. An array 346 (schematically depicted as a grid on the upper surface 344) is provided on the array board 342.

A second sensor element 350 is affixed to the arm 12 (or leg) of a patient undergoing dialysis treatment offset from the venous access sterile field 26. Adhesive or adhesive tape can be used to affix the second sensor element 350 to the arm 12 (or leg) of the patient and thus can be considered a non-sterile mounting apparatus. The array 346 is in electrical communication with the first sensor element 340 and the second sensor element 350 and is configured to communicate with a controller 352 (schematically depicted) to determine a relative position of the first sensor element 340 with respect to the second sensor element 350. The controller 352 is in electrical communication with a power source (not shown). The array 346 can include a plurality of sensors (for example at each intersection of the grid). The plurality of sensors on the array 346 are configured to communicate with both the first sensor element 340 and the second sensor element 350 and to provide a signal by way of the controller 352 to determine the location of each sensor with respect to the grid. As such, the relative distance between the first sensor element 340 and the second sensor element 350 can be determined. If the relative distance between the first sensor element 340 and the second sensor element 350 changes above a predetermined threshold, this can be an indication that the needle attached to the return line dialysis tubing 22 has dislodged. The controller 352 can then send a signal to an alarm circuit, which can generate an audible or visual indication perceptible by a human or an off signal to the pump on the dialysis machine.

Figure 9:
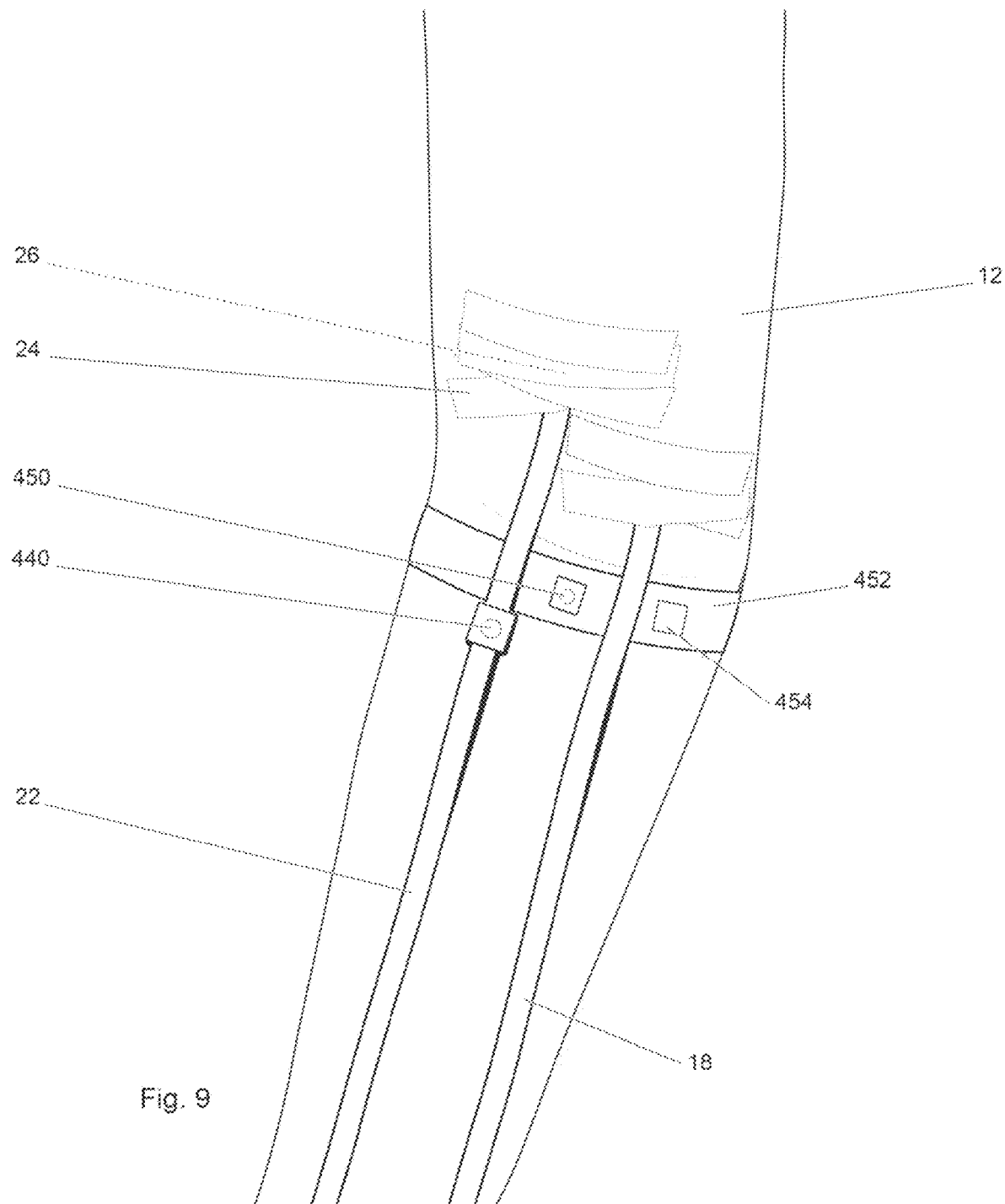
FIG. 9 is a schematic view of another system for detecting needle dislodgement.

FIG. 9 depicts another embodiment of a system for detecting needle dislodgement in which a first sensor element 440 attaches to the return line dialysis tubing 22 offset from the needle (hidden by the tape 24) and the venous access sterile field 26 in a manner such that movement of the return line dialysis tubing 22 results in movement of the first sensor element 440. A second sensor element 450 is affixed to the arm 12 (or leg) of a patient undergoing dialysis treatment offset from the venous access sterile field 26 using a cuff 452. Adhesive or adhesive tape can also be used to affix the second sensor element 450 to the arm 12 (or leg) of the patient and thus each can be considered a non-sterile mounting apparatus. In the embodiment illustrated in FIG. 9, the first sensor element 440 is configured to be positioned above the second sensor element 450 and the second sensor element 450 is configured to be positioned between the first sensor element 440 and the arm 12 (or leg) when the non-sterile sensor mounting apparatus 452, which can be a cuff, is secured to the arm 12 (or leg) and the needle at the one end of the return line dialysis tubing 22 is inserted into the venous access sterile field 26. The first sensor element 440 need not necessarily cover the second sensor element 450, but instead could be offset from but still above the second sensor element 450 in relation to the arm 12 (or leg) to facilitate placement of the return line dialysis tubing 22.

In the embodiment depicted in FIG. 9, the first sensor element 440 can be a magnet and the second sensor element 450 can be a magnetometer that measures relative change of a magnetic field at a particular location. When the second sensor element 450 is a magnetometer, it can be in electrical communication with a controller 454 (depicted schematically in FIG. 9), which is connected to a power source (not shown) such as a battery. The magnetometer can monitor the location of the first sensor element 440. When the system is turned on the relative location of the magnet with respect to the magnetometer is determined. The controller 454 can be configured, e.g., programmed, to detect a change in the location of the magnet with respect to the magnetometer that is greater than a predetermined threshold. When the controller 454 detects a change in the location of the magnet with respect to the magnetometer that is greater than the predetermined threshold, the controller 454 can generate an alarm signal similar to the alarm signal described above.

Figure 10:
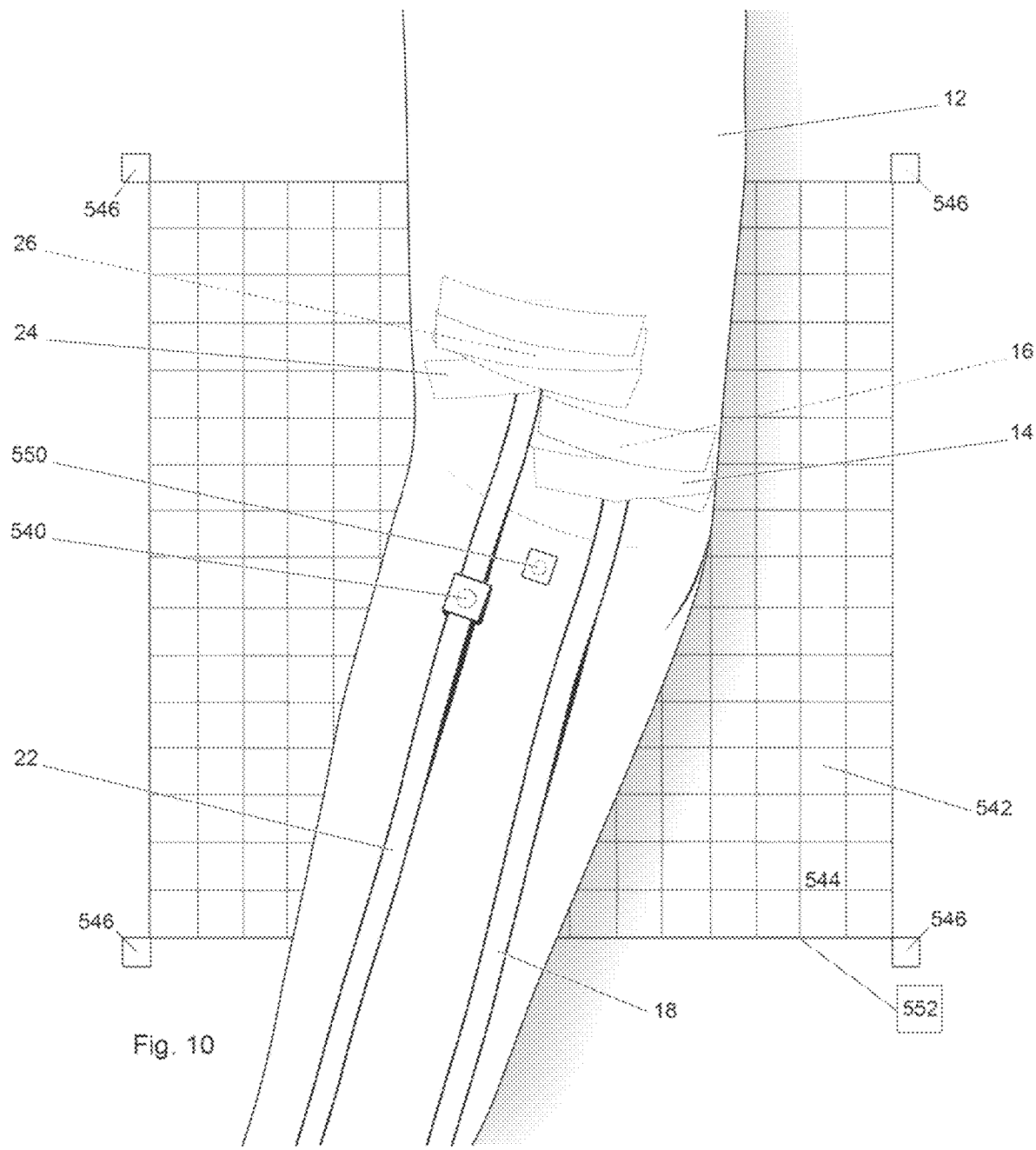
FIG. 10 is a schematic view of another system for detecting needle dislodgement.

FIG. 10 depicts another embodiment of a system for detecting needle dislodgement in which a first sensor element 540 attaches to the return line dialysis tubing 22 offset from the needle (hidden by the tape 24) and the venous access sterile field 26 in a manner such that movement of the return line dialysis tubing 22 results in movement of the first sensor element 540. A second sensor element 550 is affixed to the arm 12 (or leg) of a patient undergoing dialysis treatment offset from the venous access sterile field 26. Adhesive or adhesive tape can be used to affix the second sensor element 550 to the arm 12 (or leg) of the patient and thus each can be considered a non-sterile mounting apparatus.

Similar to the embodiment depicted in FIG. 8, an array board 542 is configured to support the arm 12 (or leg) of a patient undergoing dialysis treatment. In this embodiment, the array board 542 is also configured to support the arm 12 (or leg) offset from the venous access sterile field 26 in that the patient's arm 12 or leg rests on the array board 542 with the venous access sterile field 26 spaced from an upper surface 544 of the array board 542. At least two magnetometers 546 (four magnetometers are depicted in FIG. 10) are provided on the array board 542. Each magnetometer 546 is in electrical communication with a controller 552, which is connected to a power source (not shown) such as a battery.

In the embodiment depicted in FIG. 10, the first sensor element 540 and the second sensor element 550 are each magnets. The magnetometers 546 are each in electrical communication with the controller 554. The magnetometers 546 monitor the location of the first sensor element 540 with respect to the second sensor element 550. When the system is turned on the relative location of the first sensor element 540 with respect to the second sensor element 550 is determined. The controller 554 can be configured, e.g., programmed, to detect a change in the location of the first sensor element 540 with respect to the second sensor element 550 that is greater than a predetermined threshold. When the controller 554 detects a change in the location of the first sensor element 540 with respect to the second sensor element 550 that is greater than the predetermined threshold, the controller 554 can generate an alarm signal similar to the alarm signal described above.

Figure 11:
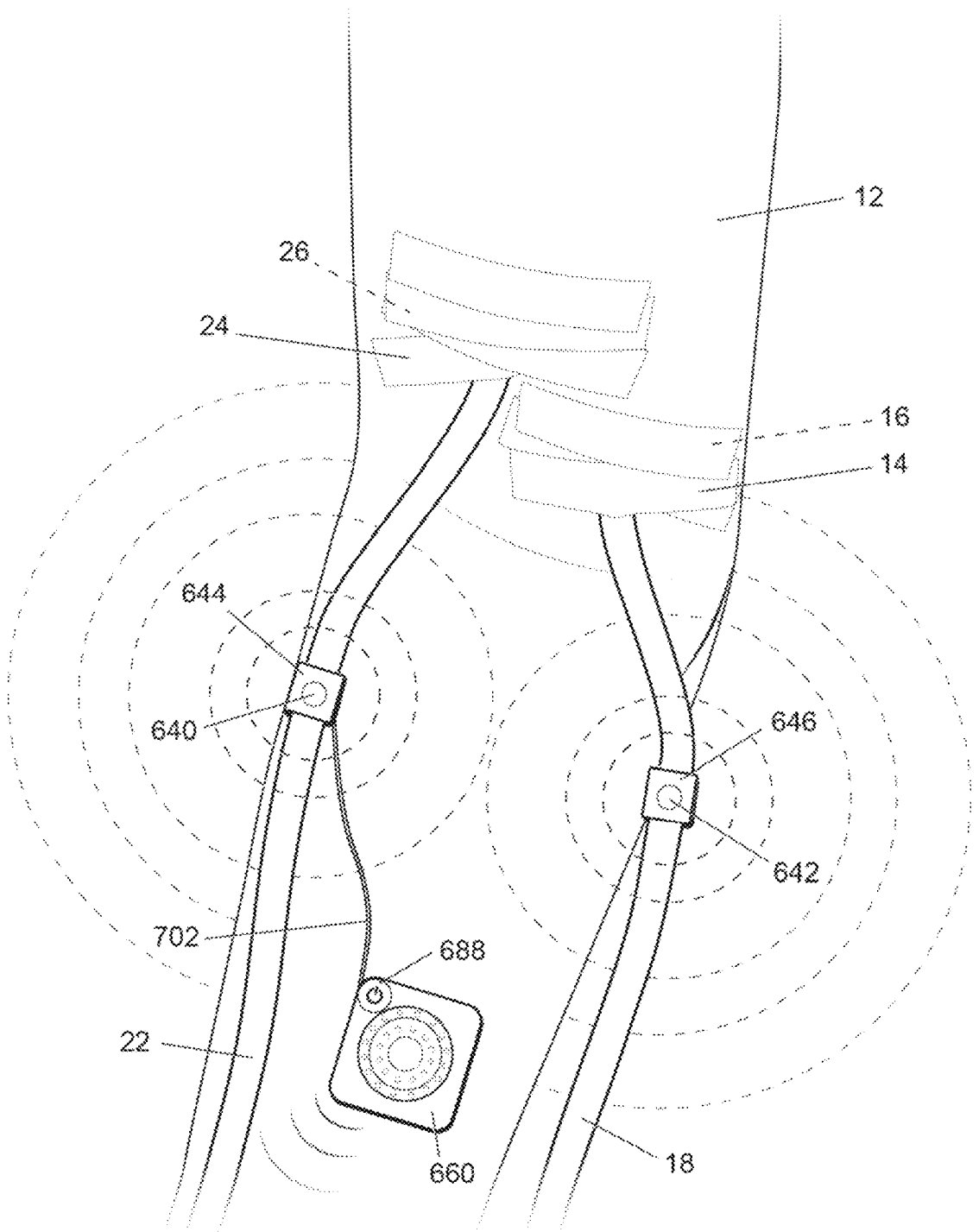
FIG. 11 is a schematic view of a system for detecting needle dislodgement according to another embodiment.
Figure 13:
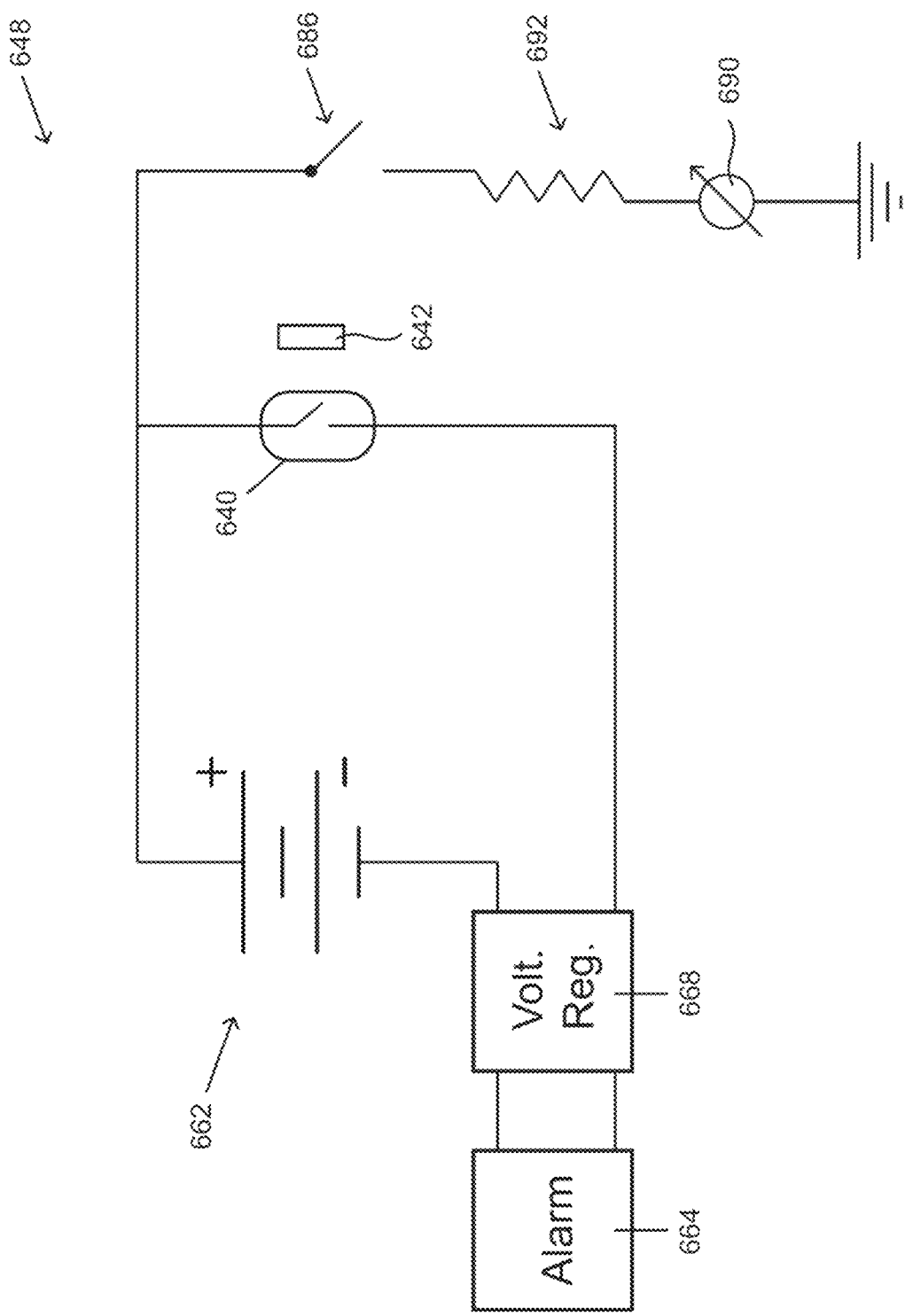
FIG. 13 is another diagram of an alarm circuit for a system for detecting needle dislodgement.

FIG. 11 depicts another embodiment of a system for detecting needle dislodgement according to yet another embodiment in which a first sensor element 640 attaches to the return line dialysis tubing 22 offset from the needle (hidden by the tape 24) and the venous access sterile field 26 in a manner such that movement of the return line dialysis tubing 22 results in movement of the first sensor element 640. A second sensor element 642 attaches to the withdrawal line dialysis tubing 18 having a needle (not shown) connected at one end offset from the sterile field 26. At least one of the sensor elements 640, 642 is in electrical communication with an alarm circuit 648 (FIG. 13). In the embodiment depicted in FIG. 11, the first sensor element 640 is in communication with the alarm circuit 648.

The first sensor element 640 can be attached to the return line dialysis tubing 22 via a first sensor element mount 644, which can be a clip or similar device carrying the first sensor element 640. Likewise, the second sensor element 642 can be attached to the withdrawal line dialysis tubing 18 via a second sensor element mount 646 carrying the second sensor element 642.

The alarm circuit 648 (FIG. 13) is configured to detect movement of the first sensor element 640 with respect to the second sensor element 642. When there is no movement outside of a predetermined threshold of the first sensor element 640 with respect to the second sensor element 642, the needle of the return line dialysis tubing 22 (and the needle of the withdrawal line dialysis tubing 18) is assumed to be properly inserted in the arm 12. However, when the movement of the first sensor element 640 with respect to the second sensor element 642 is outside the predetermined threshold, e.g., the second sensor element 642 is spaced farther than a predetermined threshold from the first sensor element 640, the needle of the return line dialysis tubing 22 (or the needle of the withdrawal line dialysis tubing 18) is assumed to have been dislodged from the arm 12. When the distance of the first sensor element 640 with respect to the second sensor element 642 is outside a predetermined threshold, the alarm circuit 648 generates a signal to a patient or caregiver indicating the needle of the return line dialysis tubing 22 (or the needle of the withdrawal line dialysis tubing 18) may be dislodged from the arm 12.

In the embodiment depicted in FIG. 11, the first sensor element 640 can be a Hall-effect sensor, a magnetometer or a Reed switch, and the second sensor element 642 can be magnet. In another embodiment (see FIG. 12), the first sensor element 640 can be a light source, and the second sensor element 642 can be a photo resistor, an infrared light receiver, or vice versa. In yet another embodiment, the first sensor element 640 can be a line of sight emitter and the second sensor element 642 can be a line of sight receiver, or vice versa. In each embodiment, the second sensor element 642 can detect the movement of the first sensor element 640 with respect to the second sensor element 642 or the first sensor element 640 can detect the movement of the second sensor element 642 with respect to the first sensor element 640.

With reference to FIG. 13, the alarm circuit 648 that is depicted is configured to generate a signal indicative of a position of the first sensor element 640 with respect to the second sensor element 642. The alarm circuit 648 is housed in a controller housing 660 (FIG. 11). A power source 662, such as a small voltage battery, can be provided in the controller housing 660. The power source 662 connects with the first sensor element 640, which can be a normally-open Reed switch. When the first sensor element 640 detects the presence of the second sensor element 642, which can be a magnet, the return line dialysis tubing 22 is in an appropriate position such that no needle dislodgement is detected. If the needle connected with the return line dialysis tubing 22 becomes dislodged, the first sensor element 640 moves with respect to the second sensor element 642, such that the first sensor element 640 no longer detects the magnetic field of the second sensor element 642, which can result in power being delivered to an alarm 664, which is part of the alarm circuit 648. An on/off switch 686, which can be operated by a button 688 on the controller housing 660, can also be provided to turn the alarm circuit 648 on and off. The alarm circuit 648 depicted in FIG. 13 also includes a light source 690 connected through a resistor 692 to the power source 662 to indicate the alarm circuit 648 is operating.

The alarm 664 can be a speaker; however, other alarms or indicators other than a speaker can also be provided. For example, a light could be illuminated. Additionally, a wireless signal generator could be provided in addition to or in lieu of the speaker to wirelessly communicate with another device, such as a smart phone or the dialysis machine, and the smart phone or dialysis machine can receive the signal and generate an appropriate indicative signal for the patient undergoing dialysis to indicate that the needle has dislodged. Additionally, the alarm circuit 648 could also provide a signal to the dialysis machine to turn off the pump when movement of the first sensor element 640 with respect to the second sensor element 642 is detected.

The alarm circuit 648 depicted in FIG. 13 is a particular example of an alarm circuit; however, the layout of the circuit may differ. Also, when sensor elements other than a Reed switch and magnet are used, then the configuration of the alarm circuit may change.

Figure 12:
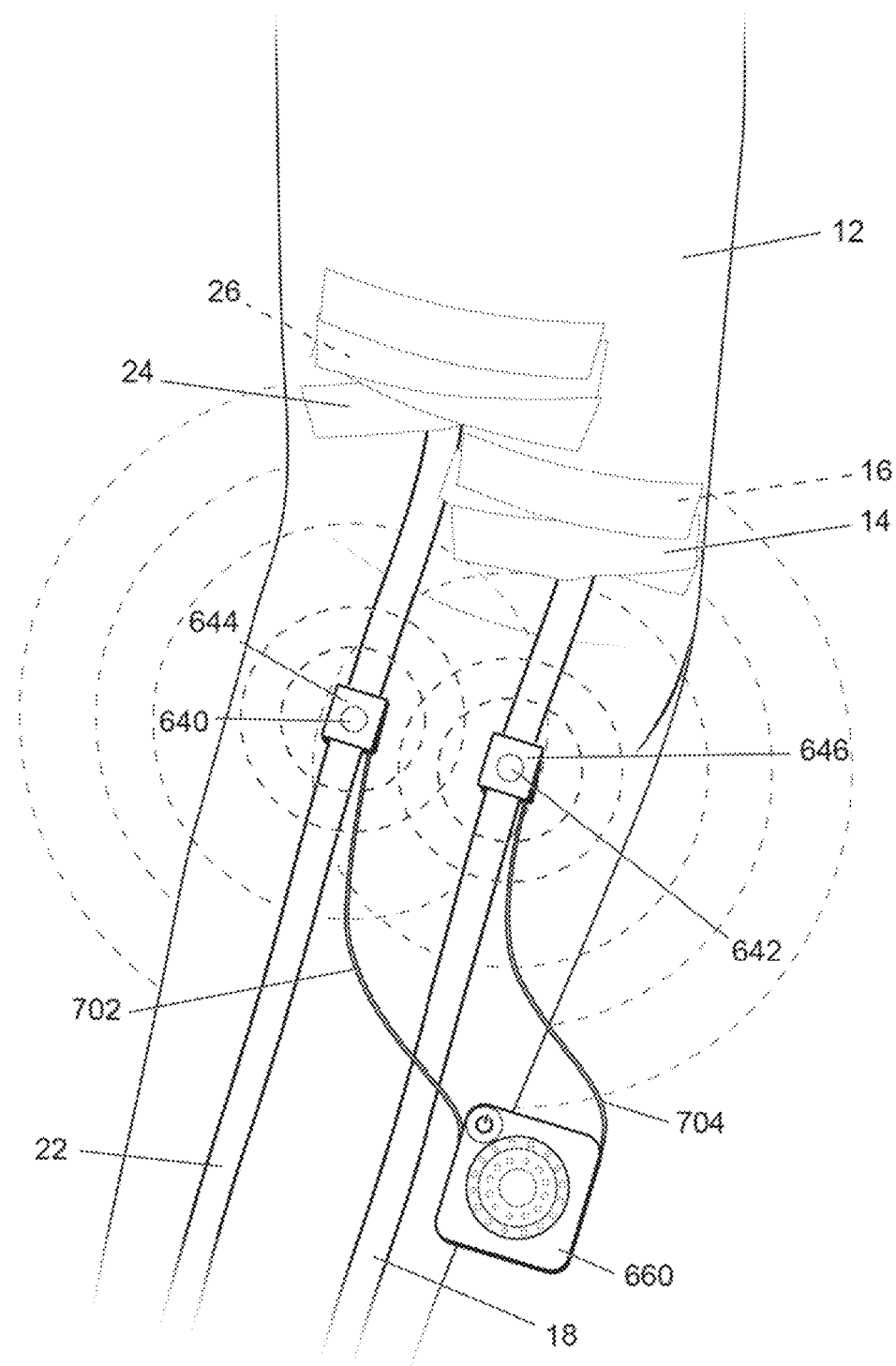
FIG. 12 is a schematic view of the system for detecting needle dislodgement depicted in FIG. 11 according to yet another embodiment.

The controller housing 660 can be connected to the first sensor element 640 via a first wire 702. The first wire 702 is receivable in the controller housing 660 and can be adjustable in length. The second sensor element 642 may also be connected to the housing 660 via a second wire 704, as depicted in FIG. 12, when the second sensor element 642 needs to receive power from the power source 662, for example when the second sensor element 642 is a photo resistor, an infrared light receiver or a line of sight receiver.

A method for detecting a needle dislodgement according to the second embodiment will be described below. First, the first sensor element 640 is attached to the return line dialysis tubing 22 having a first needle at one end so that the first sensor element 640 is offset from the first needle. Then, the second sensor element 642 is attached to the withdrawal line dialysis tubing 18 having a second needle at one end so that the second sensor element 642 is offset from the second needle. The first needle and the second needle are inserted into a patient at the sterile field 26. The movement of the first sensor element 640 with respect to the second sensor element 642 is monitored with the alarm circuit 648. When the movement of the first sensor element 640 with respect to the second sensor element 642 is outside a predetermined threshold, an alarm signal is generated via the 644 indicating a potential dislodgement of the first needle.

The first sensor element 640 can be attached to the return line dialysis tubing 22 via a first clip carrying the first sensor element 640 to the return line dialysis tubing 22 offset from the first needle and along the length of the return line dialysis tubing 22. Likewise, the second sensor element 642 may be attached to the withdrawal line dialysis tubing 18 via a second clip carrying the second sensor element 642 to the withdrawal line dialysis tubing 18 offset from the second needle and along the length of the withdrawal line dialysis tubing 18. The method may further include electrically connecting the first sensor element 640 to the controller housing 660 via the first wire 702 and electrically connecting the second sensor element 642 to the controller housing 660 via the second wire 704. Additionally, the method may also include automatically stopping the pump of the dialysis machine when the movement of the first sensor element 640 with respect to the second sensor element 642 is outside the predetermined threshold.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A system for detecting needle dislodgement comprising:
    a first sensor element configured to attach to a first associated tubing having a needle connected at one end, the first sensor element being configured to attach to the first associated tubing offset from the needle and a sterile field, which is an area on a leg or arm adjacent to where the needle is inserted, in a manner such that movement of the first associated tubing results in movement of the first sensor element,
    a second sensor element configured to attach to a second associated tubing having a needle connected at one end, the second sensor element being configured to detect movement of the first sensor element with respect to the second sensor element;
    an alarm in communication with at least one of first sensor element and the second sensor element, the alarm being configured to generate a signal when the movement of the first sensor element with respect to the second sensor element is outside a predetermined threshold;
    a first clip for attaching the first sensor element to the first associated tubing; and
    a second clip for attaching the second sensor element to the second associated tubing.

2. The system of claim 1, wherein the first sensor element is at least one of a Hall-effect sensor, a magnetometer and a Reed switch and the second sensor element is a magnet.

3. The system of claim 1, wherein the first sensor element is a light source and the second sensor element is at least one of a photo resistor and an infrared light receiver.

4. The system of claim 1, wherein the first sensor element is a line of sight emitter and the second sensor element is a line of sight receiver.

5. The system of claim 1, wherein the alarm is in communication with the first sensor element.

6. The system of claim 1, further comprising an alarm circuit in electrical communication with the first sensor element, the alarm circuit configured to generate a signal to an associated dialysis machine to disable a pump on the associated dialysis machine when the movement of the first sensor element with respect to the second sensor element is outside the predetermined threshold.

7. The system of claim 1, further comprising a controller housing in which the alarm is positioned, wherein the first sensor element is connected to the controller housing via a first wire.

8. The system of claim 7, wherein the first wire is receivable in the controller housing and adjustable in length.

9. The system of claim 7, wherein the second sensor element is connected to the controller housing via a second wire.

10. The system of claim 1, wherein the signal is a light, a buzzer, a voice recording, a vibration, a text, or a wireless message to a central system.

11. A method of detecting a needle dislodgement, the method comprising:
- attaching a first sensor element to a first associated tubing having a first needle at one end in a manner such that the first sensor element is offset from the first needle;
- attaching a second sensor element to a second associated tubing having a second needle at one end in a manner such that the second sensor element is offset from the second needle;
- inserting the first needle and the second needle into a patient at a sterile field, which is an area on a leg or arm of a patient adjacent to where the first needle and second needle are to be inserted;
- monitoring movement of the first sensor element with respect to the second sensor element using an alarm circuit; and
- generating an alarm signal via the alarm circuit when the movement of the first sensor element with respect to the second sensor element is outside a predetermined threshold indicating dislodgement of at least one of the needles.

12. The method of claim 11, wherein attaching the first sensor element to the first associated tubing further includes attaching a first clip carrying the first sensor element to the first associated tubing offset from the first needle along the length of the first associated tubing, and wherein attaching the second sensor element to the second associated tubing further includes attaching a second clip carrying the second sensor element to the second associated tubing offset from the second needle along the length of the second associated tubing offset from the second needle along the length of the second associated tubing.

13. The method of claim 12, further comprising electrically connecting the first sensor element to a controller housing via a first wire.

14. The method of claim 12, further comprising automatically stopping a pump of a dialysis machine when the movement of the first sensor element with respect to the second sensor element is outside the predetermined threshold.

* * * * *